US008821849B2

(12) United States Patent
Schwarz

(10) Patent No.: US 8,821,849 B2
(45) Date of Patent: *Sep. 2, 2014

(54) INTERNAL CLAMP FOR SURGICAL PROCEDURES

(75) Inventor: Alexander Schwarz, Brookline, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/732,781

(22) Filed: Mar. 26, 2010

(65) Prior Publication Data

US 2010/0185226 A1     Jul. 22, 2010

Related U.S. Application Data

(63) Continuation of application No. 10/983,164, filed on Nov. 5, 2004, now Pat. No. 7,700,086.

(60) Provisional application No. 60/517,929, filed on Nov. 6, 2003, provisional application No. 60/520,888, filed on Nov. 18, 2003.

(51) Int. Cl.
| *A61K 31/74* | (2006.01) |
| *A61K 9/00* | (2006.01) |
| *A61K 31/765* | (2006.01) |
| *A61K 51/12* | (2006.01) |
| *A61L 31/12* | (2006.01) |

(52) U.S. Cl.
CPC ............... *A61K 9/0024* (2013.01); *A61K 31/74* (2013.01); *A61K 31/765* (2013.01); *A61K 51/1213* (2013.01); *A61L 31/12* (2013.01)
USPC ......... 424/78.08; 424/400; 424/422; 424/426

(58) Field of Classification Search
CPC ......... A61K 31/00; A61K 31/74; A61K 9/00; A61K 9/0024; A61K 9/0002; A61K 9/0012; A61K 9/0019; A61K 9/16; A61K 9/167; A61K 51/0497; A61K 51/04; A61K 51/00; A61K 51/02; A61K 51/06; A61K 51/12; A61K 51/123; A61K 51/1217; A61K 51/1241; A61K 49/00; A61K 49/10; A61K 49/12; A61K 49/18; A61K 49/1803; A61K 2121/00; A61K 2123/00; A61L 31/10; A61L 31/16; A61L 31/00; A61L 31/04; A61L 31/041; A61L 31/08; A61L 31/12; A61L 31/125; A61L 31/14; A61L 31/145; A61L 31/148; A61L 27/54; A61L 27/58; A61L 27/00; A61L 27/14; A61L 27/40; A61L 27/44; A61L 27/48; A61L 27/50; A61L 27/52
USPC ........... 424/1.11, 1.25, 1.29, 1.33, 1.37, 1.65, 424/77, 78.08, 400, 422, 423; 623/1, 1.11, 623/1.12, 1.14, 1.17, 1.19, 1.2, 1.21, 1.42, 623/1.44, 900, 902

See application file for complete search history.

(56) References Cited

U.S. PATENT DOCUMENTS

| 3,889,685 A | 6/1975 | Miller, Jr. et al. |
| 4,168,708 A | 9/1979 | Lepley, Jr. et al. |
| 4,188,373 A | 2/1980 | Krezanoski |
| 4,268,495 A | 5/1981 | Muxfeldt et al. |
| 4,474,751 A | 10/1984 | Haslam et al. |
| 4,477,255 A | 10/1984 | Pasztor et al. |
| 4,478,822 A | 10/1984 | Haslam et al. |
| 4,551,132 A | 11/1985 | Pasztor et al. |
| 4,705,517 A | 11/1987 | DiPisa, Jr. |
| 4,795,741 A | 1/1989 | Leshchiner et al. |
| 4,819,637 A | 4/1989 | Dormandy, Jr. et al. |
| 4,946,463 A | 8/1990 | Wright |
| 4,999,188 A | 3/1991 | Solodovnik et al. |
| 5,382,260 A | 1/1995 | Dormandy, Jr. et al. |
| 5,443,478 A | 8/1995 | Purdy |
| 5,456,693 A | 10/1995 | Conston et al. |
| 5,470,568 A | 11/1995 | Lee |
| 5,476,472 A | 12/1995 | Dormandy, Jr. et al. |
| 5,514,379 A | 5/1996 | Weissleder et al. |
| 5,523,492 A | 6/1996 | Emanuele et al. |
| 5,525,334 A | 6/1996 | Ito et al. |
| 5,567,859 A | 10/1996 | Emanuele et al. |

(Continued)

FOREIGN PATENT DOCUMENTS

| CN | 1 273 860 A | 11/2000 |
| EP | 0 704 217 | 4/1996 |

(Continued)

OTHER PUBLICATIONS

Shalaby, ACS Symposium Series, American Chemical Society: Washington, D.C., 1991, pp. 502-506.*
Nonionic Surfactants: Poluoxyalkylene Block Copolymers, edited by Vaughn M. Nace, The Dow Chemical Company, Freeport, Texas, vol. 60, 1996.
Bromberg et al., "Temperature-responsive gels and thermogelling polymer matrices for protein and peptide deliver", *Advanced Drug Delivery Reviews*, 31, (1998), 197-221.
Carr, Jr., "Effects of Poloxamer 407 on the assembly, structure and dissolution of fibrin clots", *Blood Coagulation and Fibrinolysis*, vol. 7, 1996, 103-113.

(Continued)

*Primary Examiner* — D L Jones
(74) *Attorney, Agent, or Firm* — Hamilton, Brook, Smith & Reynolds, P.C.

(57) ABSTRACT

One aspect of the present invention relates to a method of occluding a vascular site in a mammal, comprising the step of introducing into the vasculature of a mammal at or proximal to a surgical site, a composition comprising at least one optionally purified inverse thermosensitive polymer, wherein said inverse thermosensitive polymer gels in said vasculature, thereby temporarily occluding a vascular site of said mammal, wherein said temporarily occluded vasculature site is kept in a substantially cylindrical shape.

2 Claims, 2 Drawing Sheets

(56) References Cited

U.S. PATENT DOCUMENTS

| | | | |
|---|---|---|---|
| 5,605,687 A | 2/1997 | Lee | |
| 5,696,298 A | 12/1997 | Emanuele et al. | |
| 5,725,552 A | 3/1998 | Kotula et al. | |
| 5,744,163 A | 4/1998 | Kim et al. | |
| 5,800,711 A | 9/1998 | Reeve et al. | |
| 5,823,198 A | 10/1998 | Jones et al. | |
| 5,834,007 A | 11/1998 | Kubota | |
| 5,843,156 A * | 12/1998 | Slepian et al. | 128/898 |
| 5,939,485 A | 8/1999 | Bromberg et al. | |
| 6,015,424 A | 1/2000 | Rosenbluth et al. | |
| 6,030,634 A | 2/2000 | Wu et al. | |
| 6,113,629 A | 9/2000 | Ken | |
| 6,120,499 A | 9/2000 | Dickens et al. | |
| 6,123,715 A | 9/2000 | Amplatz | |
| 6,165,193 A | 12/2000 | Greene, Jr. et al. | |
| 6,312,421 B1 | 11/2001 | Boock | |
| 6,316,011 B1 | 11/2001 | Ron et al. | |
| 6,333,194 B1 | 12/2001 | Levy et al. | |
| 6,355,275 B1 | 3/2002 | Klein | |
| 6,375,669 B1 | 4/2002 | Rosenbluth et al. | |
| 6,379,329 B1 | 4/2002 | Naglreiter et al. | |
| 6,403,056 B1 | 6/2002 | Unger | |
| 6,428,558 B1 | 8/2002 | Jones et al. | |
| 6,447,531 B1 | 9/2002 | Amplatz | |
| 6,464,664 B1 | 10/2002 | Jonkman et al. | |
| 6,495,579 B1 | 12/2002 | Hunter | |
| 6,500,190 B2 | 12/2002 | Greene, Jr. et al. | |
| 6,525,100 B1 | 2/2003 | Easterling et al. | |
| 6,554,849 B1 | 4/2003 | Jones et al. | |
| 6,565,527 B1 | 5/2003 | Jonkman et al. | |
| 6,579,303 B2 | 6/2003 | Amplatz | |
| 6,599,308 B2 | 7/2003 | Amplatz | |
| 6,613,074 B1 | 9/2003 | Mitelberg et al. | |
| 6,656,200 B2 | 12/2003 | Li et al. | |
| 6,660,247 B1 | 12/2003 | Gutowska et al. | |
| 6,680,046 B1 | 1/2004 | Boschetti | |
| 6,682,546 B2 | 1/2004 | Amplatz | |
| 6,686,203 B2 | 2/2004 | Calvo et al. | |
| 6,692,510 B2 | 2/2004 | West | |
| 6,723,108 B1 | 4/2004 | Jones et al. | |
| 6,761,824 B2 | 7/2004 | Reeve et al. | |
| 7,485,317 B1 | 2/2009 | Murayama et al. | |
| 7,700,086 B2 * | 4/2010 | Schwarz | 424/78.08 |
| 2001/0001835 A1 | 5/2001 | Greene, Jr. et al. | |
| 2002/0026234 A1 | 2/2002 | Li et al. | |
| 2002/0077461 A1 | 6/2002 | Bjorn et al. | |
| 2002/0103473 A1 | 8/2002 | Roychowdhury et al. | |
| 2002/0123760 A1 | 9/2002 | Amplatz | |
| 2002/0137973 A1 | 9/2002 | Reeve et al. | |
| 2002/0138095 A1 | 9/2002 | Mazzocchi et al. | |
| 2002/0141949 A1 | 10/2002 | Banerjee et al. | |
| 2002/0198561 A1 | 12/2002 | Amplatz | |
| 2003/0041602 A1 | 3/2003 | Williams, III et al. | |
| 2003/0041949 A1 | 3/2003 | Takigawa et al. | |
| 2003/0083737 A1 | 5/2003 | Greene, Jr. et al. | |
| 2003/0088311 A1 | 5/2003 | Greene, Jr. et al. | |
| 2003/0109587 A1 | 6/2003 | Mori | |
| 2003/0185896 A1 | 10/2003 | Buiser et al. | |
| 2003/0199887 A1 | 10/2003 | Ferrera et al. | |
| 2003/0211165 A1 | 11/2003 | Vogel et al. | |
| 2003/0215519 A1 | 11/2003 | Schwarz et al. | |
| 2005/0008610 A1 | 1/2005 | Schwarz et al. | |
| 2005/0147585 A1 | 7/2005 | Schwarz | |
| 2011/0076231 A1 | 3/2011 | Schwarz et al. | |
| 2013/0190814 A1 | 7/2013 | Schwarz | |
| 2013/0195753 A1 | 8/2013 | Schwarz | |

FOREIGN PATENT DOCUMENTS

| | | |
|---|---|---|
| JP | 4-264029 | 9/1992 |
| JP | 2001-329183 | 11/2001 |
| JP | 2002-531379 | 9/2002 |
| WO | WO 92/16484 | 10/1992 |
| WO | WO 00/45868 | 8/2000 |
| WO | WO 01/85845 A1 | 11/2001 |
| WO | WO 02/00193 | 1/2002 |
| WO | WO 2004/084703 A2 | 10/2004 |
| WO | WO 2005/046438 A2 | 5/2005 |

OTHER PUBLICATIONS

Blonder et al., "Dose-Dependent Hyperlipidemia in Rabbits Following Administration of Poloxamer 407 Gel", *Life Sciences*, vol. 65, No. 21, pp. PL 261-PL 266, 1991.

Matsumaru et al., "Application of thermosensitive polymers as a new embolic material for intravascular neurosurgery", *J. Biomater. Sci. Polymer Edn.*, vol. 7, No. 9, pp. 759-804 (1996).

Moghimi et al., "Poloxamers and poloxamines in nanoparticle engineering and experimental medicine", *Tibtech* Oct. 2000, vol. 18, 412-420.

Kalinoski, "Chemical Analysis of Polyoxyalkylene Block Copolymers", Nanionic Surfactants: 1996, 31-65.

Edens, "Applications of Polyoxyalkylene Block Copolymer Surfactants", Nanionic Surfactants, 1996, 185-209.

Qui et al., "Environment-sensitive hydrogels for drug delivery", *Advanced Drug Delivery Reviews*, 53 (2001), 321-339.

Barron et al., "Lipoplex-Mediated Gene Delivery to the Lung Occurs within 60 Minutes of Intravenous Administration", *Hum Gene Ther*. Jul. 1, 1999; 10 (10):1683-94.

Barron et al., "Cationic Lipids are Essential for Gene Delivery Mediated by Intravenous Administration of Lipoplexes", *Gene Ther*. Jun. 1999; 6(6):1179-83.

Cabana et al., "Study of the Gelation Process of Polyethylene Oxide.—Polypropylene Oxide$_b$—Polyethylene Oxide", Copolymer (Poloxamer 407) Aqueous Solutions. *Journal of Colloid and Interface Science* 1997; 190:307-312.

Hagstrom, "Plasmid-based Gene Delivery to Target Tissues in vivo: the Intravascular Approach", Curt Opin Mol Ther. Aug. 2003; 5(4):338-44.

Jiang et al., "Intravenous Delivery of Naked Plasmid DNA for in Vivo Cytokine Expression", *Biochem Biophys Res Commun*. Dec. 21, 2001; 289(5):1088-92.

Kabanov et al., "Pluronic Block Copolymers: Novel Functional Molecules for Gene Therapy", *Adv Drug Deliv Rev*. Feb. 21, 2000; 54(2):223-33.

Liu et al., Improving Plasmid DNA-mediated Liver Gene Transfer by Prolonging its Retention in the Hepatic Vasculature. J Gene Med. Nov.-Dec. 2001; 3(6):569-76.

Liu et al., "Hydrodynamics-based Infection in Animals by Systemic Administration of Plasmid DNA", *Gene Ther*. Jul. 1999;6(7):1258-66.

March et al., "Pharmacokinetics of Adenoviral Vector-Mediated Gene Delivery to Vascular Smooth Muscle Cells: Modulation by Poloxamer 407 and Implications for Cardiovascular Gene Therapy", *Hum Gene Ther*. 1995, 6, 41-53.

Maynard et al., "Randomized, Controlled Trial of RheothRx (poloxamer 188) in patients with suspected acute myocardial infarction", *Am Head J.* May 1998; 135 (5 Pt 1): 797-804.

Nishikawa et al., "Nonviral Vectors in the New Millennium: Delivery Barriers in Gene Transfer", *Hum Gene Ther* 20 (2001) 861-70.

O'Keefe et al., "Poloxamer-188 as an Adjunct to Primary Percutaneous Transluminal Coronary Angioplasty for Acute Myocardial Infarction", *Am J Cardiol*. Oct. 1, 1996;78(7):747-750.

Orringer et al., "Purified Poloxamer 188 for Treatment of Acute Vaso-occlusive Crisis of Sickle Cell Disease: A Randomized Controlled Trial", *JAMA* Nov. 7, 2001;286 (17):2099-2106.

Park et al., "In Situ Gelling and Mucoadhesive Polymer Vehicles for Controlled Intranasal Delivery of Plasmid DNA", *J Biomed Mater Res*. Jan. 2002; 59(1):144-51.

Pedroso et al., "Cationic Lipid-DNA Complexes in Gene Delivery: From Biophysics to Biological Applications", *Adv Drug Deliv Rev*. Apr. 25, 2001; 47(2-3):277-94.

Prokop et al., "Maximizing the In Vivo Efficiency of Gene Transfer by Means of Nonviral Polymeric Gene Delivery Vehicles", *J Pharm Sci*. Jan. 2002; 91(1):67-76.

Rocha et al., "Improvement of DNA Transfection with Cationic Liposomes", *J Physiol Biochem*. Mar. 2002; 58(1):45-56.

(56) References Cited

OTHER PUBLICATIONS

Rolland et al., "Plasmid Delivery to Muscle: Recent Advances in Polymer Delivery Systems", *Adv Drug Deliv Rev.* Mar. 2, 1998; 30(1-3):151-172.
Ron et al., "Temperature-responsive Gels and Thermogelling Polymer Matrices for Protein and Peptide Delivery", *Adv Drug Deliv Rev.* May 4, 1998;31(3):197-221.
Ross et al., "Polyethylene Glycol Enhances Lipoplex-cell Association and Lipofection", *Biochim Biophys Acta.* Oct. 15, 1999; 1421(2):273-83.
Song et al., "Enhanced Gene Expression in Mouse Lung by Prolonging the Retention Time of Intravenously Injected Plasmid DNA", *Gene Ther.* Nov. 1998; 5(11):1531-7.
Wolff et al., "Direct Gene Transfer into Mouse Muscle in Vivo", *Science* 247 (1990) 1465-1468.
Wolff et al., "Long-Term Persistence of Plasmid DNA and Foreign Gene Expression in Mouse Muscle", *Hum Mol Genet* 1(1992) 363-369.
Feigner et al., "Lipofection: A Highly Efficient, Lipid-mediated DNA-transfection Procedure", *Proc Natl Acad Sci USA* Nov. 1987: 84(21):7413-7.
Armstrong, J.K., et al., "Inhibition of Red Blood Cell-Induced Platelet Aggregation in Whole Blood by a Nonionic Surfactant, Poloxamer 188 (Rheothrx® Injection)," *Thrombosis Research*, 79(5/6): 437-450 (1995).
Berman, M.F., et al., "Determinants of Resource Utilization in the Treatment of Brain Arteriovenous Malformations," *AJNR Am. J. Neuroradiol.*, 20: 2004-2008 (1999).
Boodhwani, M., et al., "Safety and Efficacy of a Novel Gel for Vascular Occlusion in Off-Pump Surgery," *Ann. Thorac. Surg.*, 80: 2333-2337 (2005).
Carr, M.E., et al., "Effects of Poloxamer 188 on the Assembly, Structure and Dissolution of Fibrin Clots," *Thromb. Haemost.*, 66(5):565-568 (1991).
Greene, T.W., and Wuts, P.G., "Protective Groups in Organic Synthesis," A Wiley-Interscience Publication, John Wiley & Sons, Inc., NY (1991), 2$^{nd}$ Edition, ISBN 0-471-62301-6, (pp. 1-4).
Hangler, H.B., et al., "Coronary Endothelial Injury After Local Occlusion on the Human Beating Heart," *Ann. Thorac. Surg.*, 71:122-127 (2001).
Hesse, A., et al., "Study on the Prevalence and Incidence of Urolithiasis in Germany Comparing the Years 1979 vs. 2000," *Eur. Urol.*, 44(6): 709-713 (2003).
Huang, K., et al., "Synthesis and Characterization of Self-Assembling Block Copolymers Containing Bioadhesive End Groups," *Biomacromolecules*, 3: 397-406 (2002).
Jackiewicz, T.A., et al., "Structural Recovery of Small Arteries Following Clamp Injury: Alight and Electron Microscopic Investigation in the Rat," *Microsurgery*, 17(12):674-680 (1996) (Abstract Only).
Joseph, N., et al., "Angioplasty-Related Iliac Artery Rupture: Treatment by Temporary Balloon Occlusion," *Cardiovasc. Intervent. Radiol.*, 10:276-279 (1987).
Kalman, D. and Varenhorst, E., "The Role of Arterial Embolization in Renal Cell Carcinoma," *Scand. J. Urol. Nephrol.*, 33: 162-170 (1999).
Katsumori, T., et al., "Uterine Artery Embolization Using Gelatin Sponge Particles Alone for Symptomatic Uterine Fibroids: Midterm Results," *AJR*, 178: 135-139 (2002).
Labropoulos, N., et al., "Complications of the Balloon Assisted Percutaneous Transluminal Angioplasty," *J. Cardiovasc. Surg.*, 35: 475-489 (1994).
Layalle, I., et al., "Arterial Embolization of Bone Metastases: Is It Worthwhile?," *JBR-BTR*, 81: 223-225 (1998).
Lee, B.H., et al., "Synthesis and Characterization of Thermosensitive Poly(organophosphazenes) with Methoxy-Poly(ethylene glycol) and Alkylamines as Side Groups," *Bull Korean Chem. Soc.*, 23(4): 549-554 (2002).
Lee, W., et al., "Renal Angiomyolipoma: Embolotherapy with a Mixture of Alcohol and Iodized Oil," *JVIR*, 9(2): 255-261 (1998).

Manship, L.L., et al., "Differential Endothelial Injury Caused by Vascular Clamps and Vessel Loops," *The American Surgeon*, 51: 401-406 (1985).
Margovsky, A.I., et al., "Artery Wall Damage and Platelet Uptake from So-Called Atraumatic Arterial Clamps: an Experimental Study," *Cardiovascular Surgery*, 5(1): 42-47 (1997).
Margovsky, A.I., et al., "The Effect of Increasing Clamping Forces on Endothelial and Arterial Wall Damage: an Experimental Study in the Sheep," *Cardiovascular Surgery*, 7(4): 457-463 (1999).
Mitsuzaki, K., et al., "Balloon-Occluded Retrograde Transvenous Embolization of a Pelvic Arteriovenous Malformation," *Cardiovasc. Intervent. Radiol.*, 22(6):518-520 (1999).
Moore, W.M., et al., "Differential Endothelial Injury Caused by Vascular Clamps and Vessel Loops," *The American Surgeon*, 51: 392-400 (1985).
Mourikis, D., et al., "Selective Arterial Embolization in the Management of Symptomatic Renal Angiomyolipomas," *European J. of Radiology*, 32: 153-159 (1999).
Nagino, M., et al., "Right Trisegment Portal Vein Embolization for Biliary Tract Carcinoma: Technique and Clinical Utility," *Surgery*, 127(2): 155-160 (2000).
Ohta, S., et al., "Pluronic F127: Application in Arterial Embolization," *J. Vasc. Interv. Radiol.*, 17: 533-539 (2006).
Raymond, J., et al., "Temporary Vascular Occlusion with Poloxamer 407," *Biomaterials*, 25: 3983-3989 (2004).
Schmolka, I.R., et al., "A Review of Block Polymer Surfactants," *Journal of the American Oil Chemists' Society*, 54: 110-116 (1977).
Shi, H.B., et al., "Preoperative Transarterial Embolization of Spinal Tumor: Embolization Techniques and Results," *AJNR Am J Neuroradiol*, 20: 2009-2015 (1999).
Stiel, G.M., et al., "Periphere Embolie von Hamostasekollagen (VasoSeal)," *Z. Kardiol.*, 81: 543-545 (1992).
Trissel, L.A., "Handbook on Injectable Drugs, 6$^{th}$ Edition," American Society of Hospital Pharmacists, Inc. (1990) ISBN: 0-930530-98-5, (Table of Contents, pp. 1-3).
Wainwright, C.L., et al., "Inflammation as a Key Event in the Development of Neointima Following Vascular Balloon Injury," *Clinical and Experimental Pharmacology and Physiology*, 28: 891-895 (2001).
Weast, R.C., et al., "CRC Handbook of Chemistry and Physics," 70$^{th}$ Edition, CRC Press (1989-1990), (Table of Contents, pp. 1-12).
Wippermann, J., et al., "Acute Effects of Tourniquet Occlusion and Intraluminal Shunts in Beating Heart Surgery," *European Journal of Cardio-thoracic Surgery*, 24: 757-761 (2003).
International Search Report, International Application No. PCT/US04/06956, Dated: Mar. 25, 2005.
Written Opinion of the International Searching Authority, International Application No. PCT/US04/06956, Dated: Mar. 25, 2005.
International Preliminary Report on Patentability, International Application No. PCT/US2004/006956, Dated: Oct. 1, 2005.
International Search Report, International Application No. PCT/US04/36915, Dated: Apr. 10, 2006.
Written Opinion of the International Searching Authority, International Application No. PCT/US04/36915, Dated: Apr. 10, 2006.
International Preliminary Report on Patentability, International Application No. PCT/US2004/036915, Dated: May 15, 2006.
Office Action, U.S. Appl. No. 10/794,804, Dated: Jan. 4, 2007.
Office Action, U.S. Appl. No. 10/794,804, Dated: May 8, 2007.
Office Action, U.S. Appl. No. 10/794,804, Dated: Sep. 10, 2007.
Office Action, U.S. Appl. No. 10/794,804, Dated: Feb. 20, 2008.
Office Action, U.S. Appl. No. 10/794,804, Dated: Oct. 20, 2008.
Office Action, U.S. Appl. No. 10/794,804, Dated: Apr. 3, 2009.
Office Action, U.S. Appl. No. 10/983,164, Dated: Oct. 24, 2008.
Office Action, U.S. Appl. No. 10/983,164, Dated: Jun. 8, 2009.
Notice of Allowability, U.S. Appl. No. 10/983,164, Dated: Jan. 25, 2010.
Office Action, U.S. Appl. No. 12/771,735, Dated: Jun. 13, 2012.
Office Action, U.S. Appl. No. 12/771,735, Dated: Dec. 27, 2012.
Shalaby, S.W., "Thermoreversible Gels, Water-Soluble Polymers," Chapter 33: 502-506, (1991).
Office Action, U.S. Appl. No. 12/771,735, Dated: Aug. 22, 2013.

(56) References Cited

OTHER PUBLICATIONS

Office Action, U.S. Appl. No. 13/793,758, Dated Sep. 17, 2013.
Final Office Action, U.S. Appl. No. 13/242,461, Dated: Dec. 3, 2013.
Examination Report for European Application No. 13190527.5, "Temporary Embolization Using Inverse Thermosensitive Polymers", dated Mar. 27, 2014.
Communication Pursuant to Article 94(3) EPC for European Application No. 04718114.1, "Temporary Embolization Using Inverse Thermosensitive Polymers", dated Mar. 28, 2014.
Office Action, U.S. Appl. No. 12/771,735, "Temporary Embolization Using Inverse Thermosensitive Polymers", date of mailing Mar. 21, 2014.

* cited by examiner

INTERNAL CLAMP FOR SURGICAL PROCEDURES

RELATED APPLICATIONS

This application is a continuation of U.S. patent application Ser. No. 10/983,164, filed Nov. 5, 2004; which claims the benefit of priority to U.S. Provisional Patent Application Ser. No. 60/517,929, filed Nov. 6, 2003; and U.S. Provisional Patent Application Ser. No. 60/520,888, filed Nov. 18, 2003; the specifications of which are hereby incorporated in their entirety.

BACKGROUND OF THE INVENTION

Blood vessels are cut during surgical procedures. Electrocautery is effectively used to reduce or stop hemorrhaging by "burning" the bleeding blood vessels, which seals them off. Various types, shapes, and sizes of tips (probes) are available for specific treatments. A small electrode is applied to the skin near the surgical site. This is used to collect the electricity from the body and safely discharge it back to the machine. A grounding pad is placed on the person's body (usually the thigh) before the surgery starts to protect the patient. Electrocautery prevents bleeding from small sized blood vessels and capillary beds. Larger blood vessels require temporary ligation during surgery.

There are two archetypical ways to achieve temporary ligation. The first way is to ligate from the outside of a blood vessel using clamps, clips and tourniquets or snares. Such devices press against opposite sides of a flexible hollow tube so that the walls flatten out and bear against one another. This produces an axially-extending fold at the two edges. For stopping the flow of fluid through the vessel, this squeezing or pinching action is very effective. However, the lumen of these vessels have linings (intima), which should not be traumatized by strong distortions. Strong pressures, and excessive bending (axial folding), can traumatize them leading to complications after the occluder is removed.

Surgical clamps exist in many sizes with many different types of clamp shapes (e.g., curved jaws, straight jaws, etc.). In addition, many different types of jaw surfaces exist, as adapted to the specific function performed by the clamp. When a different function is to be performed, either one must use a different clamp, or in some circumstances replaceable pads may be added to the jaws. Many existing surgical clamps have jaws with hard clamping surfaces. Some replaceable pads for these clamps are designed to fit over the jaws to provide a softer clamping surface. Vascular clamps, once they are clamped to the blood vessel, are usually held in the closed position manually by the operator, or with a locking mechanism.

Clamps and clips have some shortcomings in that atherosclerotic plaque in blood vessels and calcified blood vessels do not withstand the pressure exerted by these devices. It is well known that in crossclamping of the aorta for bypass operations, plaque may be released when the clamps are opened again and the plaques may lead to strokes (Boivie P, Hansson M, Engstrom K G. "Embolic material generated by multiple aortic crossclamping: a perfusion model with human cadaveric aorta." J Thorac Cardiovasc Surg 2003 June; 125 (6): 1451-60; van der Linden J, Hadjinikolaou L, Bergman P, Lindblom D. "Postoperative stroke in cardiac surgery is related to the location and extent of atherosclerotic disease in the ascending aorta." J Am Coll Cardiol 2001 July; 38(1):131-5). In addition, especially in older patients, calcified blood vessels, when clamped, may lead to vessel damage.

A second way to achieve temporary ligation is to occlude the blood flow internally. In temporary ligation using for example balloon angioplasty, a deflated balloon catheter is placed at the arterial or venous site to be occluded; and then, the balloon is inflated, thereby blocking blood flow at the site. When the ligation is no longer necessary, the balloon may be deflated and the catheter removed (Matsuoka S, Uchiyama K, Shima H, Ohishi S, Nojiri Y, Ogata H. "Temporary percutaneous aortic balloon occlusion to enhance fluid resuscitation prior to definitive embolization of posttraumatic liver hemorrhage." Cardiovasc Intervent Radiol 2001 July-August; 24(4):274-6; Joseph N, Levy E, Lipman S. "Angioplasty-related iliac artery rupture: treatment by temporary balloon occlusion." Cardiovasc Intervent Radiol 1987; 10(5):276-9). However, the inflated balloon leads to dilation of the artery and the injury to the intima can lead to thickening and narrowing of the artery (Wainwright C L, Miller A M, Wadsworth R M. "Inflammation as a key event in the development of neointima following vascular balloon injury." Clin Exp Pharmacol Physiol 2001 November; 28(11):891-5; Labropoulos N, Giannoukas A D, Volteas S K, al Kutoubi A. "Complications of the balloon assisted percutaneous transluminal angioplasty." J Cardiovasc Surg (Torino) 1994 December; 35(6):475-89). Another way to internally occlude blood vessels is a "T" shaped device with a bulbous tip placed at either end of the "T." These devices are manufactured from silicon rubber. The bulbous tips of the device are inserted into each of the two parts of the vessel. The bulbous tips have to be the right size to effectively occlude the blood vessel. Too large and the bulbs will damage the intima, too small and the bulbs do not efficiently occlude and stop blood flow. See e.g. U.S. Pat. Nos. 3,889,685; 4,168,708; 4,946,463. In clinical practice, these devices reduce bleeding at the arteriotomy, but do not stop bleeding. The surgeon, therefore, has still to rely on additional devices like misted blowers and suction devices to clear the surgical field of blood. Further, the surgeon has to take great care not to stitch through the device and be careful during removal of the device from the arteriotomy and not entangle the device in the suture.

Consequently, there is still a need for reversibly stopping blood flow during surgery, without damage or trauma occasioned by clamps or balloons. This holds great promise in terms of, for example, patient outcome.

SUMMARY OF THE INVENTION

In certain embodiments, the present invention relates to a method of occluding a vascular site in a mammal, comprising the step of introducing into the vasculature of a mammal at or proximal to a surgical site, a composition comprising at least one optionally purified inverse thermosensitive polymer, wherein said optional purified inverse thermosensitive polymer gels in said vasculature, thereby temporarily occluding a vascular site of said mammal.

In certain embodiments, the present invention relates to a method of occluding a vascular site in a mammal, comprising the steps of introducing into the vasculature of a mammal at or proximal to a surgical site, a composition comprising at least one optionally purified inverse thermosensitive polymer, wherein said optional purified inverse thermosensitive polymer gels in said vasculature, thereby temporarily occluding a vascular site of said mammal; and performing a surgical procedure.

In certain embodiments, the present invention relates to the aforementioned method, wherein said composition comprises at least one optionally purified inverse thermosensitive polymer selected from the group consisting of poloxamers and poloxamines.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307.

In certain embodiments, the present invention relates to the aforementioned method, wherein said at least one optionally purified inverse thermosensitive polymer is poloxamer 407.

In certain embodiments, the present invention relates to the aforementioned method, wherein said temporarily occluded vascular site, at or proximal to a surgical site, is a substantially circular or substantially elliptical right cylinder, a substantially circular or substantially elliptical oblique cylinder, a substantially circular or substantially elliptical right truncated cone, or a substantially circular or substantially elliptical oblique truncated cone.

In certain embodiments, the present invention relates to the aforementioned method, wherein said composition comprises at least one optionally purified inverse thermosensitive polymer selected from the group consisting of block copolymers, random copolymers, graft polymers, and branched copolymers.

In certain embodiments, the present invention relates to the aforementioned method, wherein said at least one optionally purified inverse thermosensitive polymer is a polyoxyalkylene block copolymer.

In certain embodiments, the present invention relates to the aforementioned method, wherein said composition comprises at least one optionally purified inverse thermosensitive polymer selected from the group consisting of poloxamers and poloxamines.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307.

In certain embodiments, the present invention relates to the aforementioned method, wherein said at least one optionally purified inverse thermosensitive polymer is poloxamer 407.

In certain embodiments, the present invention relates to the aforementioned method, wherein said composition comprises at least one optionally purified inverse thermosensitive polymer selected from the group consisting of purified poloxamers and purified poloxamines.

In certain embodiments, the present invention relates to the aforementioned method, wherein said at least one optionally purified inverse thermosensitive polymer is selected from the group consisting of purified poloxamer 407, purified poloxamer 338, purified poloxamer 118, purified Tetronic® 1107 or purified Tetronic® 1307.

In certain embodiments, the present invention relates to the aforementioned method, wherein said at least one optionally purified inverse thermosensitive polymer is purified poloxamer 407.

In certain embodiments, the present invention relates to the aforementioned method, wherein said composition has a transition temperature of between about 10° C. and about 40° C.

In certain embodiments, the present invention relates to the aforementioned method, wherein said composition has a transition temperature of between about 15° C. and about 30° C.

In certain embodiments, the present invention relates to the aforementioned method, wherein the volume of said composition at physiological temperature is about 80% to about 120% of its volume below its transition temperature.

In certain embodiments, the present invention relates to the aforementioned method, wherein the volume of said composition at physiological temperature is about 80% to about 120% of its volume below its transition temperature; and said composition has a transition temperature of between about 10° C. and about 40° C.

In certain embodiments, the present invention relates to the aforementioned method, wherein the volume of said composition at physiological temperature is about 80% to about 120% of its volume below its transition temperature; and said composition has a transition temperature of between about 15° C. and about 30° C.

In certain embodiments, the present invention relates to the aforementioned method, wherein the volume of said composition at physiological temperature is about 80% to about 120% of its volume below its transition temperature; said composition has a transition temperature of between about 10° C. and about 40° C.; and said composition comprises at least one optionally purified inverse thermosensitive polymer selected from the group consisting of poloxamers and poloxamines.

In certain embodiments, the present invention relates to the aforementioned method, wherein the volume of said composition at physiological temperature is about 80% to about 120% of its volume below its transition temperature; said composition has a transition temperature of between about 15° C. and about 30° C.; and said composition comprises at least one optionally purified inverse thermosensitive polymer selected from the group consisting of poloxamers and poloxamines In certain embodiments, the present invention relates to the aforementioned method, wherein said composition comprises about 5% to about 35% of said inverse thermosensitive polymer.

In certain embodiments, the present invention relates to the aforementioned method, wherein said composition comprises about 10% to about 30% of said inverse thermosensitive polymer.

In certain embodiments, the present invention relates to the aforementioned method, wherein the inverse thermosensitive polymer has a polydispersity index from about 1.5 to about 1.0.

In certain embodiments, the present invention relates to the aforementioned method, wherein the inverse thermosensitive polymer has a polydispersity index from about 1.2 to about 1.0.

In certain embodiments, the present invention relates to the aforementioned method, wherein said surgical site is at or proximal to a hemorrhage, cancerous tissue, tumor, or organ.

In certain embodiments, the present invention relates to the aforementioned method, wherein said surgical procedure comprises anastomosis.

In certain embodiments, the present invention relates to the aforementioned method, wherein said anastomosis comprises connecting a first vessel and a second vessel.

In certain embodiments, the present invention relates to the aforementioned method, wherein said connecting a first vessel and a second vessel comprises suturing, laser welding or laser soldering.

In certain embodiments, the present invention relates to the aforementioned method, wherein said anastomosis is selected from the group consisting of end-to-end anastomosis, side-to-end anastomosis and side-to-side anastomosis.

In certain embodiments, the present invention relates to the aforementioned method, wherein said occlusion reduces bleeding during said surgical procedure.

In certain embodiments, the present invention relates to the aforementioned method, wherein said occlusion enables controlled ischemic preconditioning of said surgical site.

In certain embodiments, the present invention relates to the aforementioned method, wherein said occlusion is at or proximal to an incision site for minimally invasive surgery and decreases bleeding through the incision.

In certain embodiments, the present invention relates to the aforementioned method, wherein said composition occludes said vascular site for less than about one hour.

In certain embodiments, the present invention relates to the aforementioned method, wherein said composition further comprises a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

In certain embodiments, the present invention relates to the aforementioned method, wherein said composition further comprises a biologically active agent.

In certain embodiments, the present invention relates to the aforementioned method, wherein the biologically active agent is selected from the group consisting of antiinflammatories, antibiotics, antimicrobials, chemotherapeutics, antivirals, analgesics, antiproliferatives, plasmids, DNA and RNA.

In certain embodiments, the present invention relates to the aforementioned method, wherein said mammal is a human.

In certain embodiments, the present invention relates to the aforementioned method, wherein said composition is introduced to said vasculature through a percutaneous access device.

In certain embodiments, the present invention relates to the aforementioned method, wherein said composition is introduced to said vasculature using a catheter.

In certain embodiments, the present invention relates to the aforementioned method, wherein said composition is introduced to said vasculature using a syringe.

In certain embodiments, the present invention relates to the aforementioned method, further comprising the step of injecting an aqueous solution at or proximal to the occlusion site, thereby dissolving said occlusion.

In certain embodiments, the present invention relates to the aforementioned method, wherein said composition comprises at least one optionally purified inverse thermosensitive polymer selected from the group consisting of poloxamers and poloxamines.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307.

In certain embodiments, the present invention relates to the aforementioned method, wherein said at least one optionally purified inverse thermosensitive polymer is poloxamer 407.

In certain embodiments, the present invention relates to the aforementioned method, further comprising the step of cooling the occlusion site, thereby liquefying the gel and dissolving said occlusion.

In certain embodiments, the present invention relates to the aforementioned method, said occlusion site is cooled by using a cold aqueous solution or ice.

In certain embodiments, the present invention relates to the aforementioned method, wherein said composition comprises at least one optionally purified inverse thermosensitive polymer selected from the group consisting of poloxamers and poloxamines.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307.

In certain embodiments, the present invention relates to the aforementioned method, wherein said at least one optionally purified inverse thermosensitive polymer is poloxamer 407.

In certain embodiments, the present invention relates to the aforementioned method, wherein said composition comprises at least one optionally purified inverse thermosensitive polymer selected from the group consisting of poloxamers and poloxamines; and said surgical procedure comprises anastomosis.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307; and said surgical procedure comprises anastomosis.

In certain embodiments, the present invention relates to the aforementioned method, wherein said at least one optionally purified inverse thermosensitive polymer is poloxamer 407; and said surgical procedure comprises anastomosis.

In certain embodiments, the present invention relates to the aforementioned method, wherein said composition comprises at least one optionally purified inverse thermosensitive polymer selected from the group consisting of poloxamers and poloxamines.

In certain embodiments, the present invention relates to the aforementioned method, wherein said at least one optionally purified inverse thermosensitive polymer is selected from the group consisting of poloxamer 407, poloxamer 338, poloxamer 118, Tetronic® 1107 or Tetronic® 1307.

In certain embodiments, the present invention relates to the aforementioned method, wherein said at least one optionally purified inverse thermosensitive polymer is poloxamer 407.

DETAILED DESCRIPTION OF THE INVENTION

Definitions

Figure 1:
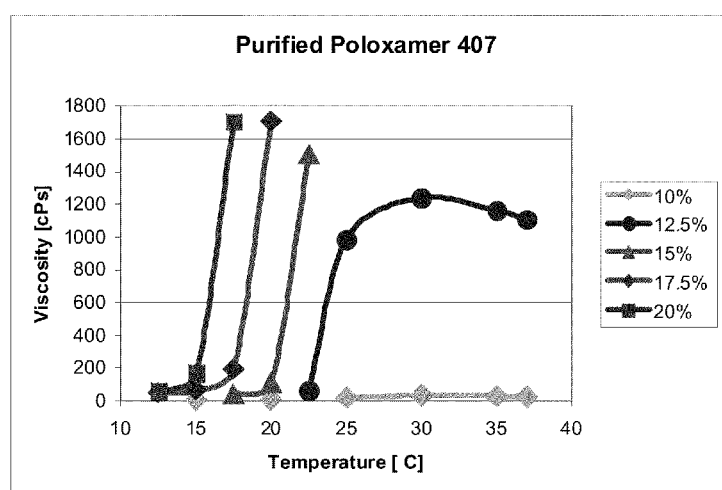
FIG. 1 depicts a graph of viscosity versus temperature for purified poloxamer 407 solutions.

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "anastomosis" as used herein refers to a surgical connection between tubular structures, such as blood vessels. "Beating heart" bypass surgeries, also known as "off-pump" bypass surgeries, are examples of surgical procedures in which anastomoses are performed.

The term "ischemia" as used herein refers to a lack of blood supply (and thus oxygen) to an organ or tissue.

The term "ischemic preconditioning" as used herein refers to a technique in which tissue is rendered resistant to the deleterious effects of prolonged ischemia by prior exposure to brief, repeated periods of vascular occlusion.

The terms "reversibly gelling" and "inverse thermosensitive" refer to the property of a polymer wherein gelation takes place upon an increase in temperature, rather than a decrease in temperature.

The term "transition temperature" refers to the temperature or temperature range at which gelation of an inverse thermosensitive polymer occurs.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

As used herein, the term "polymer" means a molecule, formed by the chemical union of two or more oligomer units. The chemical units are normally linked together by covalent linkages. The two or more combining units in a polymer can be all the same, in which case the polymer is referred to as a homopolymer. They can also be different and, thus, the polymer will be a combination of the different units. These polymers are referred to as copolymers.

The term "biocompatible", as used herein, refers to having the property of being biologically compatible by not producing a toxic, injurious, or immunological response in living tissue.

The term "degradable", as used herein, refers to having the property of breaking down or degrading under certain conditions, e.g. by dissolution.

The term "poloxamer" denotes a symmetrical block copolymer, consisting of a core of PPG polyoxyethylated to both its terminal hydroxyl groups, i.e. conforming to the interchangeable generic formula $(PEG)_X$-$(PPG)_Y$-$(PEG)_X$ and $(PEO)_X$-$(PPO)_Y$-$(PEO)_X$. Each poloxamer name ends with an arbitrary code number, which is related to the average numerical values of the respective monomer units denoted by X and Y.

The term "poloxamine" denotes a polyalkoxylated symmetrical block copolymer of ethylene diamine conforming to the general type $[(PEO)_X$-$(PPO)_Y]_2$-$NCH_2CH_2N$-$[(PPO)_Y$-$(PEO)_X]_2$. Each Poloxamine name is followed by an arbitrary code number, which is related to the average numerical values of the respective monomer units denoted by X and Y.

The phrase "polydispersity index" refers to the ratio of the "weight average molecular weight" to the "number average molecular weight" for a particular polymer; it reflects the distribution of individual molecular weights in a polymer sample.

Overview

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, reconstructive surgery and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating heart, thereby avoiding the need for a cardiopulmonary bypass.

However, in both conventional and less invasive CABG procedures, the surgeon has to connect one end of the graft vessel to the coronary artery and the other end of the graft vessel to a blood supplying vein or artery. This process is a time consuming and difficult procedure and is often further complicated by incomplete occlusion leading to blood oozing. This is especially problematic in minimally invasive surgeries where in the surgeon uses small ports to access the anatomy and robotics to perform the operation. These procedures often utilize an endoscopic camera to visualize the surgical field. When this is the case, maintaining a bloodless surgical field is especially important; a single drop of blood on the camera and the operation might have to be converted into a more invasive surgery.

Current medical practice uses a variety of devices to prevent or minimize blood oozing in the surgical practice of anastomosis. The simplest device to use would be a clamp, however, the use of clamps in arteriosclerotic vessels is dangerous due to potential dislodgement of plaque and damage to the artery. Peripherally, tourniquets are often used, e.g., in hemodialysis access surgery. A form of tourniquet commonly used in heart surgery is ligation bands, also called snares, around the artery to be bypassed. If the ligation band is tightened too tightly, damage to the artery might occur; if the ligation band is too loose, blood is still oozing out of the arteriotomy. Therefore, the surgeon has to find a compromise between visibility in the surgical field and damage to the artery.

Alternatively, an internal vessel occluder device, for example "Flo-Rester" from Synovis, Inc., which is shaped like a Q-Tip, can be inserted into the arteriotomy and mechanically occlude the artery internally. The device is extracted just prior to closing the anastomosis. However, the surgeon has to estimate the vessel diameter correctly for proper fit of the device.

Additionally, a coronary shunt can be deployed. It is shaped similarly to a Q-Tip, but with a hollow tube for blood flow through the tube. Again, the surgeon has to correctly estimate the diameter of the blood vessel for proper fit of the device. The shunts and the internal vessel occluders might be dangerous to deploy in highly arteriosclerotic vessel with heavy plaque build-up. Furthermore, these devices damage intima due to mechanical forces on the lining of the blood vessel (see e.g. Demaria R G, Fortier S, Malo O, Carrier M, Perrault L P. "Influence of intracoronary shunt size on coronary endothelial function during off-pump coronary artery bypass." Heart Surg Forum. 6 (2003)160-8; Hangler H B, Pfaller K, Ruttmann E, Hoefer D, Schachner T, Laufer G, Antretter H. "Effects of intracoronary shunts on coronary endothelial coating in the human beating heart. Ann Thorac Surg. 77 (2004) 776-80.; Demaria R G, Malo, O, Carrier, M, Perrault L P, "The Monoshunt: a new intracoronary shunt design to avoid distal endothelial dysfunction during off-pump coronary artery bypass (OPCAB)", Interact Cardiovasc Thorac Surg 2 (2003) 281-286). There are a number of other disadvantages to these internal vessel occluders: great care has to be taken during the anastomosis not to sew in the device as well as not to stitch through the device. Further, the removal of these devices is not trivial as great care has to be taken to not entangle the device in the suture.

In one embodiment of the present invention, purified, reverse thermosensitive polymers are used to occlude blood vessels during anastomosis. The purified, reverse thermosensitive polymer solution is easy to deploy by injection into the arteriotomy utilizing a syringe equipped with either a needle or a cannula. As the polymer solution quickly warms to body temperature and forms the gel plug, it prevents blood oozing due to filling of the artery with the polymer plug and provides the surgeon a clean, bloodless surgical field. Furthermore, as the gel fills the artery at the arteriotomy site, the blood vessel is kept in a cylindrical shape; contrary to all other devices used which result in flaccid blood vessels due to the emptying of the blood vessel of fluid. As the polymer is highly water-soluble, the polymer plug dissolves in blood and is excreted through the kidney. Cooling the bypass area with sterile ice or cold saline can speed up the dissolution process and enables control of the dissolution time.

In a preferred embodiment, the present invention seeks to replace the combination of inadequate products and technologies that are used by surgeons to control blood oozing during anastomosis. In these surgical procedures, bleeding is a major difficulty of the procedure. Often it is not the amount of bleeding that is dangerous for the patient, but any "oozing" makes it difficult for the surgeon to see what he is doing.

Temporarily halting blood flow in the case of hemorrhaging may also be achieved by the instant invention. Often in traumas a surgeon would benefit from halting blood flow for a short period of time to establish from where the patient is bleeding. In a preferred embodiment, the present invention seeks to halt hemorrhaging by use of a thermosensitive polymer plug as described herein.

The instant invention may be applied to all surgical procedures, which involve the connection of two blood vessels, e.g., coronary bypass, peripheral bypass, hemodialysis access (creation of a fistula), and free-flap surgery (breast and face reconstruction surgery). The instant invention may aid in the establishment of end to end, side to end and side to side anastomoses.

Interestingly, a number of devices, existing or under development, aim at simplifying bypass surgery by automating the sewing of arteries to each other, or eliminating sewing altogether. They are sometimes called anastomosis devices. Far from competing with the instant invention, these devices require perfectly cylindrical blood vessels to interact with. Unlike clamps or snares, which can flatten and damage the artery, the method of the instant invention maintains the cylindrical shape of the artery once it is filled with gel, a feature that is very attractive to the suppliers of anastomosis devices.

Laser welding has been shown to work as an alternative to suturing, however, the process is made more difficult by the need to have a cylindrical vessel. Since an artery occluded with gel maintains its cylindrical shape, an additional advantage to the instant occlusion method is that alternatives to traditional suturing, such as laser soldering or welding, may be performed. While various inventors have proposed devises, e.g., an albumin hollow tube to be inserted into the anastomosis site to keep the artery cylindrical, the instant invention will dramatically ease the technical difficulty of these suturing alternatives.

Methods of the Invention

In a preferred embodiment, the present invention significantly simplifies anastomosis by assuring a bloodless surgical field, obviates the surgeon from having to guess the size of the artery at the arteriotomy site, and maintains a substantially cylindrical shape of said artery, by injecting temporary plugs in the vessels being joined thereby occluding said vessels. The plugs consist of an aqueous solution of inverse thermosensitive polymers. These polymer solutions are soft gels at about 20° C. and as they are injected into the body the gels further stiffens to form hard gels at about body temperature. The polymer solution starts externally of the body and thus at a temperature below body temperature.

Introduction/Removal of the Plug

In one embodiment, the polymer solution can be introduced through a catheter. Said catheter can be a dual or multi-lumen catheter. In one embodiment, the catheter is 3-10 French in size, and more preferably 3-6 French.

In another embodiment, a syringe used to inject the inverse thermosensitive polymer into the body can be, for example, a 0.1-10 cc syringe or a syringe with volume of 1-3 cc or with a volume of 0.1-1 cc. Pressure applied to the syringe can be applied by hand or by an automated syringe pusher (see Example 2 below).

The gelation of reverse thermosensitive polymers is dependent on the temperature and the concentration of the polymer. Therefore, after the anastomosis procedure, the gel can be removed by instilling a fluid around the gel, which leads to dissolution of the gel. The fluid may be chilled to help in the dissolution with a preferred temperature of about 10° C. below the gelation temperature. The fluid can be instilled through a catheter or syringe percutaneously. Alternatively, the site of the anastomosis can be chilled by placing sterile ice on the procedure site, thereby cooling the gel to below its gelation temperature. The liquid polymer dilutes in blood and is washed away from the anastomosis.

Inverse Thermosensitive Polymers

In general, the inverse thermosensitive polymers used in the methods of the invention, which become a gel at or about body temperature, can be injected into the patient's body in a liquid or soft gel form. The injected material once reaching body temperature undergoes a transition from a liquid or soft gel to a hard gel. The inverse thermosensitive polymers used in connection with the methods of the invention may comprise a block copolymer with inverse thermal gelation properties. In general, biocompatible, biodegradable block copolymers that exist as a gel at body temperature and a liquid at below body temperature may also be used according to the present invention. Also, the inverse thermosensitive polymer can include a therapeutic agent such as anti-angiogenic agents, hormones, anesthetics, antimicrobial agents (antibacterial, antifungal, antiviral), anti-inflammatory agents, diagnostic agents, or wound healing agents. Similarly, low concentrations of dye (such as methylene blue) or fillers can be added to the inverse thermosensitive polymer.

The molecular weight of the inverse thermosensitive polymer is preferably between 1,000 and 50,000, more preferably between 5,000 and 35,000. Preferably the polymer is in an aqueous solution. For example, typical aqueous solutions contain about 5% to about 30% polymer, preferably about 10% to about 25%. The molecular weight of a suitable inverse thermosensitive polymer (such as a poloxamer or poloxamine) may be, for example, between 5,000 and 25,000, and more particularly between 7,000 and 20,000.

The pH of the inverse thermosensitive polymer formulation administered to the mammal is, generally, about 6.0 to about 7.8, which are suitable pH levels for injection into the mammalian body. The pH level may be adjusted by any suitable acid or base, such as hydrochloric acid or sodium hydroxide.

Poloxamers (Pluronics)

Notably, Pluronic® polymers have unique surfactant abilities and extremely low toxicity and immunogenic responses. These products have low acute oral and dermal toxicity and low potential for causing irritation or sensitization, and the general chronic and sub-chronic toxicity is low. In fact, Pluronic® polymers are among a small number of surfactants that have been approved by the FDA for direct use in medical applications and as food additives (BASF (1990) Pluronic® & Tetronic® Surfactants, BASF Co., Mount Olive, N.J.). Recently, several Pluronic® polymers have been found to enhance the therapeutic effect of drugs, and the gene transfer efficiency mediated by adenovirus. (March K L, Madison J E, Trapnell B C. "Pharmacokinetics of adenoviral vector-mediated gene delivery to vascular smooth muscle cells: modulation by poloxamer 407 and implication for cardiovascular gene therapy" *Hum Gene Therapy* 1995, 6, 41-53).

Poloxamers (or Pluronics), as nonionic surfactants, are widely used in diverse industrial applications. (Nonionic Surfactants: polyoxyalkylene block copolymers, Vol. 60. Nace V M, Dekker M (editors), New York, 1996. 280 pp.) Their surfactant properties have been useful in detergency, dispersion, stabilization, foaming, and emulsification. (Cabana A, Abdellatif A K, Juhasz J. "Study of the gelation process of polyethylene oxide. polypropylene oxide-polyethylene oxide copolymer (poloxamer 407) aqueous solutions." Journal of Colloid and Interface Science. 1997; 190: 307-312.) Certain poloxamines, e.g., poloxamine 1307 and 1107, also display inverse thermosensitivity.

Some of these polymers have been considered for various cardiovascular applications, as well as in sickle cell anemia. (Maynard C, Swenson R, Paris J A, Martin J S, Hallstrom A P, Cerqueira M D, Weaver W D. Randomized, controlled trial of RheothRx (poloxamer 188) in patients with suspected acute myocardial infarction. RheothRx in Myocardial Infarction Study Group. Am Heart J. 1998 May; 135 (5 Pt 1): 797-804; O'Keefe J H, Grines C L, DeWood M A, Schaer G L, Browne K, Magorien R D, Kalbfleisch J M, Fletcher W O Jr, Bateman T M, Gibbons R J. Poloxamer-188 as an adjunct to primary percutaneous transluminal coronary angioplasty for acute myocardial infarction. Am J Cardiol. 1996 Oct. 1; 78(7):747-750; and Orringer E P, Casella J F, Ataga K I, Koshy M, Adams-Graves P, Luchtman-Jones L, Wun T, Watanabe M, Shafer F, Kutlar A, Abboud M, Steinberg M, Adler B, Swerdlow P, Terregino C, Saccente S, Files B, Ballas S, Brown R, Wojtowicz-Praga S, Grindel J M. Purified poloxamer 188 for treatment of acute vasoocclusive crisis of sickle cell disease: A randomized controlled trial. JAMA. 2001 Nov. 7; 286 (17):2099-2106.)

Importantly, several members of this class of polymer, poloxamer 188, poloxamer 407, poloxamer 338, poloxamines 1107 and 1307 show inverse thermosensitivity within the physiological temperature range. (Qiu Y, Park K. Environment-sensitive hydrogels for drug delivery. Adv Drug Deliv Rev. 2001 Dec. 31; 53(3):321-339; and Ron E S, Bromberg L E Temperature-responsive gels and thermogelling polymer matrices for protein and peptide delivery Adv Drug Deliv Rev. 1998 May 4; 31(3):197-221.) In other words, these polymers are members of a class that are soluble in aqueous solutions at low temperature, but gel at higher temperatures. Poloxamer 407 is a biocompatible polyoxypropylene-polyoxyethylene block copolymer having an average molecular weight of about 12,500 and a polyoxypropylene fraction of about 30%; poloxamer 188 has an average molecular weight of about 8400 and a polyoxypropylene fraction of about 20%; poloxamer 338 has an average molecular weight of about 14,600 and a polyoxypropylene fraction of about 20%; poloxamine 1,107 has an average molecular weight of about 14,000, poloxamine 1307 has an average molecular weight of about 18,000. Polymers of this type are also referred to as reversibly gelling because their viscosity increases and decreases with an increase and decrease in temperature, respectively. Such reversibly gelling systems are useful wherever it is desirable to handle a material in a fluid state, but performance is preferably in a gelled or more viscous state. As noted above, certain poly(ethyleneoxide)/poly(propyleneoxide) block copolymers have these properties; they are available commercially as Pluronic® poloxamers and Tetronic® poloxamines (BASF, Ludwigshafen, Germany) and generically known as poloxamers and poloxamines, respectively. See U.S. Pat. Nos. 4,188,373, 4,478,822 and 4,474,751.

The average molecular weights of the poloxamers range from about 1,000 to greater than 16,000 daltons. Because the poloxamers are products of a sequential series of reactions, the molecular weights of the individual poloxamer molecules form a statistical distribution about the average molecular weight. In addition, commercially available poloxamers contain substantial amounts of poly(oxyethylene) homopolymer and poly(oxyethylene)/poly(oxypropylene diblock polymers. The relative amounts of these byproducts increase as the molecular weights of the component blocks of the poloxamer increase. Depending upon the manufacturer, these byproducts may constitute from about 15 to about 50% of the total mass of the polymer.

Purification of Inverse Thermosensitive Polymers

The inverse thermosensitive polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

In certain embodiments, a purified poloxamer or poloxamine has a polydispersity index from about 1.5 to about 1.0. In certain embodiments, a purified poloxamer or poloxamine has a polydispersity index from about 1.2 to about 1.0.

The aforementioned process consists of forming an aqueous two-phase system composed of the polymer and an appropriate salt in water. In such a system, a soluble salt can be added to a single phase polymer-water system to induce phase separation to yield a high salt, low polymer bottom phase, and a low salt, high polymer upper phase. Lower molecular weight polymers partition preferentially into the high salt, low polymer phase. Polymers that can be fractionated using this process include polyethers, glycols such as poly(ethylene glycol) and poly(ethylene oxide)s, polyoxyalkylene block copolymers such as poloxamers, poloxamines, and polyoxypropylene/polyoxybutylene copolymers, and other polyols, such as polyvinyl alcohol. The average molecular weight of these polymers may range from about 800 to greater than 100,000 daltons. See U.S. Pat. No. 6,761, 824. The aforementioned purification process inherently exploits the differences in size and polarity, and therefore solubility, among the poloxamer molecules, the poly(oxyethylene) homopolymer and the poly(oxyethylene)/poly(oxypropylene) diblock byproducts. The polar fraction of the poloxamer, which generally includes the lower molecular weight fraction and the byproducts, is removed allowing the higher molecular weight fraction of poloxamer to be recovered. The larger molecular weight poloxamer recovered by this method has physical characteristics substantially different from the starting material or commercially available poloxamer including a higher average molecular weight, lower polydispersity and a higher viscosity in aqueous solution.

Other purification methods may be used to achieve the desired outcome. For example, WO 92/16484 discloses the use of gel permeation chromatography to isolate a fraction of poloxamer 188 that exhibits beneficial biological effects, without causing potentially deleterious side effects. The copolymer thus obtained had a polydispersity index of 1.07 or less, and was substantially saturated. The potentially harmful side effects were shown to be associated with the low molecular weight, unsaturated portion of the polymer, while the medically beneficial effects resided in the uniform higher molecular weight material. Other similarly improved copolymers were obtained by purifying either the polyoxypropylene center block during synthesis of the copolymer, or the copolymer product itself (e.g., U.S. Pat. No. 5,523,492 and U.S. Pat. No. 5,696,298).

Further, a supercritical fluid extraction technique has been used to fractionate a polyoxyalkylene block copolymer as disclosed in U.S. Pat. No. 5,567,859. A purified fraction was obtained, which was composed of a fairly uniform polyoxyalkylene block copolymer having a polydispersity of less than 1.17. According to this method, the lower molecular weight fraction was removed in a stream of carbon dioxide maintained at a pressure of 2200 pounds per square inch (psi) and a temperature of 40° C.

Additionally, U.S. Pat. No. 5,800,711 discloses a process for the fractionation of polyoxyalkylene block copolymers by the batchwise removal of low molecular weight species using a salt extraction and liquid phase separation technique. Poloxamer 407 and poloxamer 188 were fractionated by this method. In each case, a copolymer fraction was obtained which had a higher average molecular weight and a lower polydispersity index as compared to the starting material. However, the changes in polydispersity index were modest and analysis by gel permeation chromatography indicated that some low-molecular-weight material remained. The viscosity of aqueous solutions of the fractionated polymers was significantly greater than the viscosity of the commercially available polymers at temperatures between 10° C. and 37° C., an important property for some medical and drug delivery applications. Nevertheless, some of the low molecular weight contaminants of these polymers are thought to cause deleterious side effects when used inside the body, making it especially important that they be removed in the fractionation process. As a consequence, polyoxyalkylene block copolymers fractionated by this process are not appropriate for all medical uses.

As mentioned above, the use of these polymers in larger concentrations in humans requires removal of lower molecular weight contaminants present in commercial preparations. As was demonstrated in U.S. Pat. No. 5,567,859 (Examples 8 & 9), the lower molecular weight contaminants are mostly responsible for the toxic effects seen. In a clinical trial using unpurified poloxamer 188, an unacceptable level of transient renal dysfunction was found (Maynard C, Swenson R, Paris J A, Martin J S, Hallstrom A P, Cerqueira M D, Weaver W D. Randomized, controlled trial of RheothRx (poloxamer 188) in patients with suspected acute myocardial infarction. RheothRx in Myocardial Infarction Study Group. Am Heart J. 1998 May; 135(5 Pt 1):797-804), while another clinical trial using purified poloxamer 188 specifically mentioned that no renal dysfunction was found (Orringer E P, Casella J F, Ataga K I, Koshy M, Adams-Graves P, Luchtman-Jones L, Wun T, Watanabe M, Shafer F, Kutlar A, Abboud M, Steinberg M, Adler B, Swerdlow P, Terregino C, Saccente S, Files B, Ballas S, Brown R, Wojtowicz-Praga S, Grindel J M. Purified poloxamer 188 for treatment of acute vasoocclusive crisis of sickle cell disease: A randomized controlled trial. JAMA. 2001 Nov. 7; 286(17):2099-2106.) Therefore, it seems imperative to utilize only fractionated poloxamers and poloxamines in vascular applications like the ones envisioned here. Furthermore, fractionation of these thermosensitive polymers leads to improved gels with stronger mechanical resistance and due to the improved thermosensitivity requires less polymer to achieve gelation (See for example U.S. Pat. No. 6,761,824 on a purification scheme and the resultant viscosities).

Anastomosis in Conjunction with Drug Delivery

Effective therapeutic use of many types of biologically active molecules has not been achieved simply because methods are not available to cause delivery of therapeutically effective amounts of such substances into the particular cells of a patient for which treatment would provide therapeutic benefit. Efficient delivery of therapeutically sufficient amounts of such molecules into cells has often proved difficult, if not impossible, since, for example, the cell membrane presents a selectively-permeable barrier. Additionally, even when biologically active molecules successfully enter targeted cells, they may be degraded directly in the cell cytoplasm or even transported to structures in the cell, such as lysosomal compartments, specialized for degradative processes. Thus, both the nature of substances that are allowed to enter cells, and the amounts thereof that ultimately arrive at targeted locations within cells, at which they can provide therapeutic benefit, are strictly limited.

Although such selectivity is generally necessary in order that proper cell function can be maintained, it comes with the disadvantage that many therapeutically valuable substances (or therapeutically effective amounts) are excluded. Additionally, the complex structure, behavior, and environment presented by an intact tissue that is targeted for intracellular delivery of biologically active molecules often interfere substantially with such delivery, in comparison with the case presented by populations of cells cultured in vitro. Therefore, new ways of delivering drugs at the right time, in a controlled manner, with minimal side effects, and greater efficacy per dose are sought by the drug-delivery and pharmaceutical industries.

The reversibly gelling polymers used in the anastomosis methods of the invention have physico-chemical characteristics that make them suitable delivery vehicles for conventional small-molecule drugs, as well as new macromolecular (e.g., peptides) drugs or other therapeutic products. Therefore, the composition comprising the thermosensitive polymer may further comprise a pharmaceutic agent selected to provide a pre-selected pharmaceutic effect. A pharmaceutic effect is one which seeks to treat the source or symptom of a disease or physical disorder. Pharmaceutics include those products subject to regulation under the FDA pharmaceutic guidelines, as well as consumer products. Importantly, the compositions used anastomosis methods of the invention are capable of solubilizing and releasing bioactive materials. Solubilization is expected to occur as a result of dissolution in the bulk aqueous phase or by incorporation of the solute in micelles created by the hydrophobic domains of the poloxamer. Release of the drug would occur through diffusion or network erosion mechanisms.

Those skilled in the art will appreciate that the compositions used in the anastomosis methods of the invention may simultaneously be utilized to deliver a wide variety of pharmaceutic and personal care applications. To prepare a pharmaceutic composition, an effective amount of pharmaceutically active agent(s), which imparts the desirable pharmaceutic effect is incorporated into the reversibly gelling composition used in the anastomosis methods of the invention. Preferably, the selected agent is water soluble, which will readily lend itself to a homogeneous dispersion throughout the reversibly gelling composition. It is also preferred that the agent(s) is non-reactive with the composition. For materials, which are not water soluble, it is also within the scope of the anastomosis methods of the invention to disperse or suspend lipophilic material throughout the composition. Myriad bioactive materials may be delivered using the methods of the present invention; the delivered bioactive material includes anesthetics, antimicrobial agents (antibacterial, antifungal, antiviral), anti-inflammatory agents, diagnostic agents, and wound healing agents.

Because the reversibly gelling composition used in the methods of the present invention are suited for application under a variety of physiological conditions, a wide variety of pharmaceutically active agents may be incorporated into and administered from the composition. The pharmaceutic agent loaded into the polymer networks of the thermosensitive polymer may be any substance having biological activity, including proteins, polypeptides, polynucleotides, nucleoproteins, polysaccharides, glycoproteins, lipoproteins, and synthetic and biologically engineered analogs thereof.

A vast number of therapeutic agents may be incorporated in the polymers used in the methods of the present invention. In general, therapeutic agents which may be administered via the methods of the invention include, without limitation: anti-infectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. Suitable pharmaceuticals for parenteral administration are well known as is exemplified by the Handbook on Injectable Drugs, 6$^{th}$ Edition, by Lawrence A. Trissel, American Society of Hospital Pharmacists, Bethesda, Md., 1990 (hereby incorporated by reference).

The pharmaceutically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. The pharmaceutical agents may be selected from insulin, antigens selected from the group consisting of MMR (mumps, measles and rubella) vaccine, typhoid vaccine, hepatitis A vaccine, hepatitis B vaccine, herpes simplex virus, bacterial toxoids, cholera toxin B-subunit, influenza vaccine virus, bordetela pertussis virus, vaccinia virus, adenovirus, canary pox, polio vaccine virus, *plasmodium falciparum, bacillus calmette geurin* (BCG), *klebsiella pneumoniae*, HIV envelop glycoproteins and cytokins and other agents selected from the group consisting of bovine somatropine (sometimes referred to as BST), estrogens, androgens, insulin growth factors (sometimes referred to as IGF), interleukin I, interleukin II and cytokins Three such cytokins are interferon-β, interferon-γ and tuftsin.

Examples of bacterial toxoids that may be incorporated in the compositions used in the occlusion methods of the invention are tetanus, diphtheria, pseudomonas A, *mycobaeterium tuberculosis*. Examples of that may be incorporated in the compositions used in the occlusion methods of the invention are HIV envelope glycoproteins, e.g., gp 120 or gp 160, for AIDS vaccines. Examples of anti-ulcer H2 receptor antagonists that may be included are ranitidine, cimetidine and famotidine, and other anti-ulcer drugs are omparazide, cesupride and misoprostol. An example of a hypoglycaemic agent is glizipide.

Classes of pharmaceutically active compounds which can be loaded into that may be incorporated in the compositions used in the occlusion methods of the invention include, but are not limited to, anti-AIDS substances, anti-cancer substances, antibiotics, immunosuppressants (e.g., cyclosporine) anti-viral substances, enzyme inhibitors, neurotoxins, opioids, hypnotics, antihistamines, lubricants tranquilizers, anti-convulsants, muscle relaxants and anti-Parkinson substances, antispasmodics and muscle contractants, miotics and anticholinergics, anti-glaucoma compounds, anti-parasite and/or anti-protozoal compounds, anti-hypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

Exemplary pharmaceutical agents considered to be particularly suitable for incorporation in the compositions used in the occlusion methods of the invention include but are not limited to imidazoles, such as miconazole, econazole, terconazole, saperconazole, itraconazole, metronidazole, fluconazole, ketoconazole, and clotrimazole, luteinizing-hormone-releasing hormone (LHRH) and its analogues, nonoxynol-9, a GnRH agonist or antagonist, natural or synthetic progestrin, such as selected progesterone, 17-hydroxyprogeterone derivatives such as medroxyprogesterone acetate, and 19-nortestosterone analogues such as norethindrone, natural or synthetic estrogens, conjugated estrogens, estradiol, estropipate, and ethinyl estradiol, bisphosphonates including etidronate, alendronate, tiludronate, resedronate, clodronate, and pamidronate, calcitonin, parathyroid hormones, carbonic anhydrase inhibitor such as felbamate and dorzolamide, a mast cell stabilizer such as xesterbergsterol-A, lodoxamine, and cromolyn, a prostaglandin inhibitor such as diclofenac and ketorolac, a steroid such as prednisolone, dexamethasone, fluromethylone, rimexolone, and lotepednol, an antihistamine such as antazoline, pheniramine, and histiminase, pilocarpine nitrate, a beta-blocker such as levobunolol and timolol maleate. As will be understood by those skilled in the art, two or more pharmaceutical agents may be combined for specific effects. The necessary amounts of active ingredient can be determined by simple experimentation.

By way of example only, any of a number of antibiotics and antimicrobials may be included in the thermosensitive polymers used in the methods of the invention. Antimicrobial drugs preferred for inclusion in compositions used in the occlusion methods of the invention include salts of lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine and the like.

By way of example only, in the case of anti-inflammation, non-steroidal anti-inflammatory agents (NSAIDS) may be incorporated in the compositions used in the occlusion methods of the invention, such as propionic acid derivatives, acetic acid, fenamic acid derivatives, biphenylcarboxylic acid derivatives, oxicams, including but not limited to aspirin, acetaminophen, ibuprofen, naproxen, benoxaprofen, flurbiprofen, fenbufen, ketoprofen, indoprofen, pirprofen, carporfen, and bucloxic acid and the like.

Occlusion in Conjunction with Gene Therapy

Another application of the compositions and methods described in the instant invention would be to aid in the delivery of a wide variety growth factors or gene therapeutic agents. Although defective genes associated with numerous inherited diseases (or that represent disease risk factors, including cancer risk factors) have been isolated and characterized, methods to correct the disease states themselves, by providing patients with normal copies of such genes (the technique of gene therapy), are substantially lacking By way of example only, diseases that it is hoped may be treated by gene therapy include inherited disorders such as cystic fibrosis, hemophilias, Gaucher's disease, Fabry's disease, and muscular dystrophy (myopathy). Again by way of example, acquired disorders that can be treated include cancer (e.g., multiple myeloma, leukemias, melanomas, ovarian carcinoma and small cell lung cancer), cardiovascular conditions (e.g., progressive heart failure, restenosis), and neurological conditions (e.g., traumatic brain injury).

Gene therapy requires successful transfection of target cells in a patient. Transfection may generally be defined as the process of introducing an expressible natural or synthetic polynucleotide (e.g., a gene, a cDNA, or a mRNA) into a cell. Successful expression of the encoding polynucleotide leads to production in the cells of a normal protein and leads to correction of the disease state associated with the abnormal gene. Therapies based on providing such proteins directly to target cells (protein replacement therapy) are often ineffective as methods are not available to cause delivery of therapeutically effective amounts of such substances into the particular cells of a patient for which treatment would provide therapeutic benefit.

Early in the 1990s, Wolff et al showed that transfection is achievable using "naked DNA" injected into muscle (Wolff, J A, et al, Direct Gene Transfer into Mouse Muscle in Vivo", Science 247 (1990) 1465-1468; Wolff et al, Long-Term persistence of plasmid DNA and foreign gene expression in mouse muscle", Hum Mol Genet 1 (1992) 363-369). This transfection method usually leads to a transient expression of the encoded proteins. Furthermore, due to the highly localized nature of the injection, only local areas of gene expression might be achieved. This is highly disadvantageous in disease like Duchenne's disease, for example, in which the whole or large parts of the diaphragm needs to be transfected to achieve a cure. Further, the transduction levels achieved with naked DNA are not sufficiently high for therapeutic use.

It was earlier discovered that addition of transfection agents increased the transfection rate and therefore, the expression level. There are numerous transfection agents that have been described in the literature (Felgner P L, Gadek T R, Holm M, Roman R, Chan H W, Wenz M, Northrop J P, Ringold G M, Danielsen M., Lipofection: a highly efficient, lipid-mediated DNA-transfection procedure. Proc Natl Acad Sci USA. 1987 November; 84(21):7413-7. for reviews: Rocha A, Ruiz S, Coll J M., Improvement of DNA transfection with cationic liposomes. J Physiol Biochem. 2002 March; 58(1):45-56; Pedroso de Lima M C, Simoes S, Pires P, Faneca H, Duzgunes N., Cationic lipid-DNA complexes in gene delivery: from biophysics to biological applications. Adv Drug Deliv Rev. 2001 Apr. 25; 47(2-3):277-94). Further dramatic improvements in transfection efficiencies were discovered when using non-ionic polymers in combination with transfection agents (Rolland A P, Mumper R J., Plasmid delivery to muscle: Recent advances in polymer delivery systems. Adv Drug Deliv Rev. 1998 Mar. 2; 30(1-3):151-172; Nishikawa, M, Huang, L., Nonviral vectors in the new millennium: delivery barriers in gene transfer, Hum Gene Ther 20 (2001) 861-70; Ross P C, Hui S W., Polyethylene glycol enhances lipoplex-cell association and lipofection. Biochim Biophys Acta. 1999 Oct. 15; 1421(2):273-83). Among non-charged polymers discovered to improve the transfection were poloxamers and poloxamines (Prokop A, Kozlov E, Moore W, Davidson J M., Maximizing the in vivo efficiency of gene transfer by means of nonviral polymeric gene delivery vehicles. J Pharm Sci. 2002 January; 91(1):67-76.; Kabanov A V, Lemieux P, Vinogradov S, Alakhov V. Pluronic block copolymers: novel functional molecules for gene therapy. Adv Drug Deliv Rev. 2002 Feb. 21; 54(2):223-33; Park J S, Oh Y K, Yoon H, Kim J M, Kim C K. In situ gelling and mucoadhesive polymer vehicles for controlled intranasal delivery of plasmid DNA. J Biomed Mater Res. 2002 January; 59(1):144-51).

It has also been noted that physical effects can increase the rate of transfection. Liu et al demonstrated a simple method of intravascular gene transfection by injection of large volumes of DNA containing solutions into the tail of mice (Liu F, Song Y, Liu D. Hydrodynamics-based transfection in animals by systemic administration of plasmid DNA. Gene Ther. 1999 July; 6(7):1258-66.; Jiang J, Yamato E, Miyazaki J. Intravenous delivery of naked plasmid DNA for in vivo cytokine expression. Biochem Biophys Res Commun. 2001 Dec. 21; 289(5):1088-92.). They termed this method hydrodynamic transfection. Presumably the increase in transfection versus control is due to an increase in pressure in the blood vessels, increasing the permeability of the cell walls.

A similar effect was discovered by Song et al when the retention time was increased in the vasculature (Song Y K, Liu F, Liu D. Enhanced gene expression in mouse lung by prolonging the retention time of intravenously injected plasmid DNA. Gene Ther. 1998 November; 5(11):1531-7). The increase in retention was achieved by injecting the liposomes prior to the injection of the naked DNA. As the liposomes increase in size due aggregation caused by different components in blood, they reach the size of capillaries and temporarily occlude the blood vessels. An increase in DNA retention time in the lung results in a higher level of gene expression in the targeted lung area. Controls using naked DNA without prior injection of liposomes did not enhance gene transfer (Barron L G, Uyechi L S, Szoka F C Jr., Cationic lipids are essential for gene delivery mediated by intravenous administration of lipoplexes. Gene Ther. 1999 June; 6(6): 1179-83). These results suggest that prolonging the exposure time of DNA to the target cells in vivo may be an important strategy in achieving a high level of gene expression.

While Song et al utilized liposomes to increase the DNA retention in the target area, Liu and Huang used surgery to reach the target area and utilized clamps to temporarily stop blood flow and increase the residence time of the DNA in the target vasculature (Liu F, Huang L, Improving plasmid DNA-mediated liver gene transfer by prolonging its retention in the hepatic vasculature. J Gene Med. 2001 November-December; 3(6):569-76). They stopped blood flow for a very short time and demonstrated that effective gene transfer occurred. Barron et al also showed that the gene transfer occurs rather rapidly within less than 60 minutes after injection of the lipoplexes (Barron L G, Gagne L, Szoka F C Jr. Lipoplex-mediated gene delivery to the lung occurs within 60 minutes of intravenous administration. Hum Gene Ther. 1999 Jul. 1; 10(10):1683-94).

However the gene therapy approach described by Liu and Huang (surgical clamping, prior to injection of liposomes) is not practical in a clinical setting, as it would be preferable to introduce the polynucleotide via a catheter or a syringe. It is well understood that liposome-mediated or naked DNA gene transfection can be successfully performed to all vessel layers or muscles in vivo by using a local delivery catheter (Hagstrom J E. Plasmid-based gene delivery to target tissues in vivo: the intravascular approach. Curr Opin Mol Ther. 2003 August; 5(4):338-44). However, unwanted transfection at a distance may occur with catheter-based local delivery and therefore a device is needed to occlude the target area to achieve an increase in retention time. While this could be achieved by using a balloon catheter and the injection through the balloon, balloon angioplasty is known to lead to arterial damage and even rupture of the artery (Wainright C L, Miller A M, Wadsworth R M., Inflammation as a key event in the development of neointima following vascular balloon injury. Clin Exp Pharmacol Physiol. 2001 November; 28(11): 891-5; Labropoulos N, Giannoukas A D, Volteas S K, al Kutoubi A., Complications of the balloon assisted percutaneous transluminal angioplasty. Review article. J Cardiovasc Surg (Torino). 1994 December; 35(6):475-89).

In a preferred embodiment the methods and compositions of the instant invention can be used to temporarily occlude a blood vessel, either independently our in conjunction with a surgical procedure such as anastomosis, prior to or concurrently with the introduction of nucleic acids behind the occlusion, thereby increasing the residence time of nucleic acids in an intravascular target area. The nucleic acids are then injected through the gel by either a syringe or a catheter and the nucleic acid are retained behind the gel in the target area. If the occlusion is on the venous side, the nucleic acid is injected in the arterial side and as there is no drainage until the gel erodes, the nucleic acids are retained on the arterial side. Alternatively, both proximal and distal sites from the target area may be occluded with a reverse thermosensitive polymer composition of the instant invention. As described above, the polynucleotide can be "naked" or complexed into lipoplexes constituting nucleic acids, cationic lipids, and optionally helper lipids.

In certain embodiments, the present invention relates to the aforementioned method, in which a reverse thermosensitive polymer is injected into a blood vessel proximally to the target area, in vivo, in such a way that the mixture gels and temporarily and reversibly occludes the vascular site and the nucleic acid is injected through the gel into the stagnant blood of the target area.

In certain embodiments, the present invention relates to the aforementioned method, in which a reverse thermosensitive polymer is injected into a blood vessel proximally and distally to the target area, in vivo, in such a way that the mixture gels and temporarily and reversibly occludes the vascular site and the nucleic acid is injected through the gel on the proximal side into the stagnant blood of the target area.

In certain embodiments, the present invention relates to the aforementioned method, in which a reverse thermosensitive polymer is injected distally from the target area, in such a way as to occlude blood drainage from the target area and nucleic acids or a nucleic acid complex are injected into a blood vessel proximally to the target area.

In certain embodiments, the present invention relates to the aforementioned methods, in which a reverse thermosensitive polymer is injected into a blood vessel proximally to the target area, in vivo, in such a way that it gels and temporarily and reversibly occludes the vascular site, and a nucleic acid is injected into the same blood vessel at the same time.

In certain embodiments, the present invention relates to the aforementioned method, in which a reverse thermosensitive polymer is injected distally from the target area, in such a way as to occlude blood drainage from the target area and nucleic acids or a nucleic acid complex are injected in a hypertonic solution into a blood vessel proximally to the target area.

In certain embodiments, the present invention relates to the aforementioned method, in which a reverse thermosensitive polymer is injected distally from the target area, in such a way as to occlude blood outflow from the target area and nucleic acids or a nucleic acid complex are injected hydrodynamically into a blood vessel proximally to the target area.

In certain embodiments, the present invention relates to the aforementioned method, in which the nucleic acid is injected at the same time as the occlusion of the blood vessel.

In certain embodiments, the present invention relates to the aforementioned method, in which the nucleic acid is injected within less than about one minute after occlusion of the blood vessel.

In certain embodiments, the present invention relates to the aforementioned method, in which the nucleic acid is injected within less than about ten minutes after occlusion of the blood vessel.

In certain embodiments, the present invention relates to the aforementioned method, wherein the nucleic acid is a plasmid, cDNA, mRNA and PNA.

In certain embodiments, the present invention relates to the aforementioned method, wherein the nucleic acid is not complexed ("naked").

In certain embodiments, the present invention relates to the aforementioned method, wherein the nucleic acid is complexed with cationic lipids into lipoplexes.

In certain embodiments, the present invention relates to the aforementioned method, wherein the nucleic acid is complexed with cationic lipids and helper lipids into lipoplexes.

In certain embodiments, the present invention relates to the aforementioned method, wherein said composition is introduced into the vasculature of said mammal using a catheter.

In certain embodiments, the present invention relates to the aforementioned method, wherein said composition is introduced into the vasculature of said mammal using a syringe.

EXEMPLIFICATION

The invention now being generally described, it will be more readily understood by reference to the following examples, which are included merely for purposes of illustration of certain aspects and embodiments of the present invention, and are not intended to limit the invention.

Example 1

In-Vitro Testing and Principal of Operation

The viscosity changes were measured in a Brookfield Cone and Cup viscometer with temperature control. A graph of the viscosity changes (FIG. 1) clearly shows polymer concentrations from approximately 12.5 w % until at least 20 w % will show steep increases in solution viscosities with temperature. The onset of gelation is dependent on the temperature and higher polymer concentrations lead to earlier onsets of gelation. Furthermore, polymer concentrations below approximately 12.5 w % do not demonstrate an increase in solution viscosity with temperature and remain liquid even at body temperature.

These two findings demonstrate the potential operation principle of the purified poloxamer 407. The polymer solution is injected as a soft gel at the temperature of a typical OR (about 18° C.) into the arteriotomy and the rise in temperature leads to a stiff gel. The gel will start to dissolve in blood and when the concentration of the polymer decreases below approximately 12.5%, it turns back into a liquid, without any possibility to turn back into a gel at physiological temperatures. Alternatively, cooling of the gel with ice or cold saline would liquefy the gel as the temperature falls below the gelation point. As a liquid, it quickly dilutes in blood and again there is no possibility for it to turn back into a gel at physiological temperatures.

Example 2

Injectability of Purified Poloxamer 407 through Various Needle Gauges

A three milliliter polycarbonate syringe (Merrit Medallion) was loaded in the cold with three milliliter of 20 w % purified poloxamer 407. Various sized needles were attached via a luer lock and the injectability of the polymer solution was tested at 6° C. (liquid state) and at room temperature (23° C.; soft gel state) as shown in the table below.

TABLE 1

Injectability of 20 w % purified poloxamer 407 through a 3 mL syringe

| Needle | 6° C. | 23° C. |
| --- | --- | --- |
| 16G | easy | easy |
| 18G | easy | easy |

TABLE 1-continued

Injectability of 20 w % purified poloxamer 407 through a 3 mL syringe

| Needle | 6° C. | 23° C. |
| --- | --- | --- |
| 21G | easy | easy |
| 25G | easy | pushable |
| 27G | easy | required hard push |

The same experiment was repeated using a one milliliter polycarbonate syringe (Merrit Medallion) and in all cases, the polymer could be easily injected through the various needle gauges.

TABLE 2

Injectability of 20 w % purified poloxamer 407 through a 1 mL syringe

| Needle | 6° C. | 23° C. |
| --- | --- | --- |
| 16G | easy | easy |
| 18G | easy | easy |
| 21G | easy | easy |
| 25G | easy | easy |
| 27G | easy | easy |

Example 3

In-Vivo Feasibility Animal Trial: Occlusion Experiments

The experiments described below were conducted in pigs. A segment of the distal half of the LAD was selected for the experiment. The diameter of the LAD varied from about 1 to 2 millimeter. An ultrasound flow probe was placed distally from the injection site around the LAD. A one milliliter syringe equipped with a 27 G needle was used to inject approximately 200 µL of 20 w % purified poloxamer 407 into the LAD. Flow stopped immediately as evidenced by the flow probe. The occlusion remained between 6 minutes and 18 minutes, averaging approximately 9 minutes. Blood flow was reestablished immediately after the occlusion dissolved, a typical hyperemic response was seen with an approximate doubling of the blood flow. Blood flow returned to normal values within 20 minutes.

Example 4

In-Vivo Feasibility Animal Trial: Arteriotomy Experiments

The experiments described below were conducted in three mongrel dogs. A segment of the distal half of the LAD was selected for the anastomostic site. Silicone Elastic tapes were passed deep to the LAD approximately 2 cm apart, flanking the chosen site. A Genzyme Immobilizer OP-CAB stabilizer was positioned to stabilize the LAD and the tapes snared to transiently interrupt coronary flow. The Immobilizer was left in position for 3 minutes to provide pre-ischemic conditioning, so that the animal would subsequently tolerate longer periods of regional ischemia. After 3 minutes, the tapes were loosened to allow reperfusion. After an additional 5 minutes of reperfusion, the tapes were snared once again, and the cycle repeated two additional times.

After 3 cycles of pre-ischemic conditioning, the Silicone-Elastic tapes were snared and the LAD arteriotomy created. In this acute animal model, hemostasis was excellent, given the elastic nature of disease-free coronaries, and the lack of collaterals in the absence of coronary stenosis or occlusion. Therefore, the proximal tape was loosened slightly until modest bleeding occurred, approximating the amount of bleeding seen in difficult anastomosis. About one milliliter of a 20 w % solution of purified poloxamer 407 was instilled into the coronary through the arteriotomy via a cannula to improve hemostasis. Bleeding stopped immediately and the surgical field was bloodless. The arteriotomy was not sutured and the site started rebleeding after approximately 17 minutes. The experiment was repeated at the same site and rebleeding occurred after approximately 19 minutes.

All three dogs underwent the same procedure and could be evaluated. The occluded site on the LAD was excised and evaluated by histology. Neither ischemic damage nor early necrosis was detected and normal myocardium was found.

Example 5

In-Vivo Feasibility Animal Trial: Control of Dissolution Time

The same experiment as described above was performed on the LAD of a mongrel dog and approximately 0.6 milliliter of a 20 w % purified poloxamer 407 solution was injected into the arteriotomy via a cannula. Bleeding stopped immediately. The gel kept the artery in a cylindrical shape and the lids of the arteriotomy were clearly visible. Suturing was performed through the gel and was completed within 7 minutes. The LAD was still occluded and small amounts of sterile ice were placed on the LAD at the occlusion site to convert the polymer plug back into solution. The LAD opened up again nearly instantaneously. This experiment demonstrated A) the possibility to control the occlusion time by using ice placed onto the arteriotomy. This is a very important feature as surgeons would want to be able to reopen the occlusion should something go wrong during the surgery and blood flow is needed. And B) that gel keeps the artery in a cylindrical shape during the occlusion, making suturing very easy.

Example 6

In-Vivo Feasibility Animal trial: Comparison of Blood Loss with Snares, and Snares & 20 w % Purified Poloxamer 407 Gel The following experiments were conducted in 4 pigs. The goal of the experiment was to measure blood loss as a distinction between ligation bands and polymer plug. Further, the patency of the graft was evaluated by fluoroscopy after utilizing the polymer plug for the anastomosis.

The same approach for OPCAB was used as described above to create the acute animal model with some modifications as described below.

The Immobilizer was modified by attaching a drape to make a shallow well that captured all coronary blood and allowed the amount of bleeding from the arteriotomy to be quantified.

After 3 cycles of pre-ischemic conditioning, as described above, the Silicone-Elastic tapes were snared and the LAD arteriotomy created. At this point, the adequacy of hemostasis was assessed. The proximal tape was loosened slightly until modest bleeding occurred, comparable to what is generally encountered clinically.

While maintaining blood pressure, the bleeding was allowed to continue for 15 minutes to approximate the time required for a distal anastomosis. During these 15 minutes, blood that accumulated in the modified stabilizer well was drawn intermittently through a syringe and measured in a volumetric cylinder. After the 15 minutes had passed, a shunt was deployed in the LAD for 20 minutes to allow for reperfusion of the myocardium. After reperfusion, the tapes were again tightened to very similar tension as before, bleeding out of the arteriotomy was assured and blood pressure was maintained.

Approximately 300 µL of the purified poloxamer 407 at the temperature of the OR (about 18° C.) was instilled upstream and approximately 100 µL downstream into the coronary through the arteriotomy site using a cannula. With the polymer gel in place, any blood that accumulated in the stabilizer basin was removed by syringe. In contrast to the dog experiments, the arteriotomy opened again between 6.5 and 8.5 minutes and in each case, approximately 100 µL of the purified poloxamer 407 was instilled upstream again. In two animals, a third application after about 13 to 14 minutes, of approximately 100 µL was needed to provide the bloodless surgical field. Most of the blood collected during the application of the purified poloxamer 407 was deemed to stem from the snare holes, but blood volume collected was not corrected for this in the gel experiments as well as the tape experiments. After 15 minutes, the remaining blood was removed and added to that previously collected to quantify total arteriotomy blood loss for the 15 minutes with purified poloxamer 407 in place. The order of vessel occlusion was reversed for two animals with the gel first, followed by the tapes.

Figure 2:
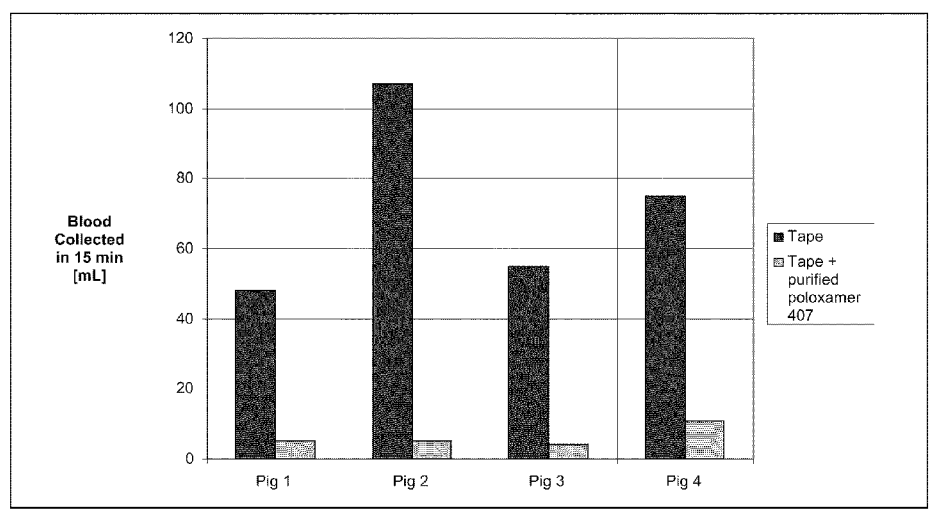
FIG. 2 depicts a graph of blood volume collected from an anastomosis site with and without purified poloxamer 407.

The volume of blood captured during the two 15 minute periods, with and without internal vessel occlusion with purified poloxamer 407, were compared and are shown in FIG. 2. The application of purified poloxamer 407 reduces bleeding by approximately 90% in the four animals.

The graft was sutured onto the arteriotomy with either the gel present or the tapes utilized and after two additional hours, fluoroscopy was used to evaluate patency of the graft. In three pigs in which the evaluation could be performed, the grafts were patent. Euthanasia was administered under anesthesia. A sample of subtended myocardium was harvested and sent for histology to assess for myocardial ischemia or early necrosis. Normal myocardium was found by histological evaluation.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of temporarily occluding a vascular site in a mammal, comprising the steps of: introducing into the vasculature of a mammal, at or proximal to a surgical site, a composition comprising at least one purified inverse thermosensitive polymer selected from poloxamer 407, poloxamer 338, poloxamer 118, polamine 1107 or poloxamine 1307, wherein said purified inverse thermosensitive polymer gels in said vasculature; maintaining a bloodless surgical site temporarily; and performing a surgical procedure.

2. The method of claim 1, further comprising the step of dissolution of the polymer.

\* \* \* \* \*